(12) United States Patent
Torrione (10) Patent No.: US 12,338,723 B2
(45) Date of Patent: Jun. 24, 2025

(54) SYSTEM AND METHOD FOR MEASURING CHARACTERISTICS OF CUTTINGS FROM DRILLING OPERATIONS WITH COMPUTER VISION

(71) Applicant: HELMERICH & PAYNE TECHNOLOGIES, LLC, Tulsa, OK (US)

(72) Inventor: Peter A. Torrione, Durham, NC (US)

(73) Assignee: HELMERICH & PAYNE TECHNOLOGIES, LLC, Tulsa, OK (US)

(*) Notice: Subject to any disclaimer, the term of this patent is extended or adjusted under 35 U.S.C. 154(b) by 0 days.

(21) Appl. No.: 18/754,956

(22) Filed: Jun. 26, 2024

(65) Prior Publication Data

US 2024/0344442 A1    Oct. 17, 2024

Related U.S. Application Data

(63) Continuation of application No. 17/808,986, filed on Jun. 25, 2022, now Pat. No. 12,049,812, which is a
(Continued)

(51) Int. Cl.
*E21B 44/00*    (2006.01)
*E21B 21/06*    (2006.01)
(Continued)

(52) U.S. Cl.
CPC ............ *E21B 44/00* (2013.01); *E21B 21/065* (2013.01); *E21B 49/005* (2013.01);
(Continued)

(58) Field of Classification Search
CPC ...... E21B 44/00; E21B 21/065; E21B 49/005; G01N 15/0227; G01N 33/24; G05B 15/02
See application file for complete search history.

(56) References Cited

U.S. PATENT DOCUMENTS

| 4,610,005 A | 9/1986 | Utasi |
| 4,794,534 A | 12/1988 | Millheim |

(Continued)

FOREIGN PATENT DOCUMENTS

| CN | 102621150 A | 8/2012 |
| JP | 05242737 | 9/1993 |

(Continued)

OTHER PUBLICATIONS

U.S. Appl. No. 14/938,962, "Final Office Action", Jul. 19, 2018, 10 pages.

(Continued)

*Primary Examiner* — Charles R Kasenge
(74) *Attorney, Agent, or Firm* — Kilpatrick Townsend & Stockton LLP (57) ABSTRACT

System and method for monitoring cuttings from drilling. The method comprising acquiring a plurality of images from a camera oriented to face at least a portion of a screen surface of a shaker having drilling mud or cuttings thereon from a well during drilling; detecting a plurality of particles from the plurality of images; obtaining data associated with the plurality of particles; and modeling a statistical distribution of particles based at least in part on the data associated with the plurality of particles. The method further comprising monitoring the statistical distribution of particles over time; determining a change in a likelihood of the monitored statistical distribution of particles based at least in part on the modeled statistical distribution of particles; and providing an alert if the change in the likelihood of the monitored statistical distribution of particles falls outside a threshold range.

20 Claims, 4 Drawing Sheets

Related U.S. Application Data continuation of application No. 16/749,588, filed on Jan. 22, 2020, now Pat. No. 11,408,266, which is a continuation of application No. 14/938,962, filed on Nov. 12, 2015, now Pat. No. 10,577,912.

(60) Provisional application No. 62/212,233, filed on Aug. 31, 2015, provisional application No. 62/212,252, filed on Aug. 31, 2015, provisional application No. 62/078,573, filed on Nov. 12, 2014.

(51) Int. Cl.
    *E21B 49/00*     (2006.01)
    *G01N 15/0227*     (2024.01)
    *G01N 33/24*     (2006.01)
    *G05B 15/02*     (2006.01)

(52) U.S. Cl.
    CPC ......... *G01N 15/0227* (2013.01); *G01N 33/24* (2013.01); *G05B 15/02* (2013.01)

(56) References Cited

U.S. PATENT DOCUMENTS

| | | |
|---|---|---|
| 6,256,046 B1 | 7/2001 | Waters et al. |
| 6,469,734 B1 | 10/2002 | Nichani et al. |
| 6,646,676 B1 | 11/2003 | DaGraca et al. |
| 7,874,351 B2 | 1/2011 | Hampton et al. |
| 7,933,166 B2 | 4/2011 | Goodman |
| 8,136,690 B2 | 3/2012 | Fang et al. |
| 8,138,690 B2 | 3/2012 | Chemel et al. |
| 8,218,826 B2 | 7/2012 | Ciglenec et al. |
| 8,233,667 B2 | 7/2012 | Helgason et al. |
| 8,363,101 B2 | 1/2013 | Gschwendtner et al. |
| 8,395,661 B1 | 3/2013 | Olsson et al. |
| 8,528,660 B2 | 9/2013 | Santos |
| 8,547,428 B1 | 10/2013 | Olsson et al. |
| 8,622,128 B2 | 1/2014 | Hegeman |
| 8,746,459 B2 | 6/2014 | Scott et al. |
| 8,812,236 B1 | 8/2014 | Freeman et al. |
| 8,873,806 B2 | 10/2014 | Kiest, Jr. |
| 9,016,399 B2 | 4/2015 | Pelletier et al. |
| 9,041,794 B1 | 5/2015 | Olsson et al. |
| 9,134,255 B1 | 9/2015 | Olsson et al. |
| 9,149,840 B2 | 10/2015 | Dahl |
| 9,175,557 B2 | 11/2015 | Iversen et al. |
| 9,279,319 B2 | 3/2016 | Savage |
| 9,410,877 B2 | 8/2016 | Maxey et al. |
| 9,464,492 B2 | 10/2016 | Austefjord et al. |
| 9,498,796 B2 | 11/2016 | Dahl |
| 9,518,817 B2 | 12/2016 | Baba et al. |
| 9,651,468 B2 | 5/2017 | Rowe et al. |
| 9,664,011 B2 | 5/2017 | Kruspe et al. |
| 9,677,882 B2 | 6/2017 | Kiest, Jr. |
| 9,706,185 B2 | 7/2017 | Ellis |
| 9,869,145 B2 | 1/2018 | Jones et al. |
| 9,912,918 B2 | 3/2018 | Samuel |
| 9,915,112 B2 | 3/2018 | Geehan et al. |
| 10,151,677 B2 | 12/2018 | Kulkarni et al. |
| 10,227,859 B2 | 3/2019 | Richards et al. |
| 10,328,503 B2 | 6/2019 | Osawa et al. |
| 10,577,912 B2 | 3/2020 | Torrione |
| 11,408,266 B2 | 8/2022 | Torrione |
| 12,049,812 B2 | 7/2024 | Torrione |
| 2005/0135667 A1 | 6/2005 | Saarela et al. |
| 2006/0162962 A1 | 7/2006 | Koederitz et al. |
| 2007/0165225 A1 | 7/2007 | Trainer |
| 2007/0221410 A1 | 9/2007 | Butler et al. |
| 2007/0221411 A1 | 9/2007 | Butler et al. |
| 2008/0123937 A1 | 5/2008 | Arias Estrada et al. |
| 2008/0162085 A1 | 7/2008 | Clayton et al. |
| 2009/0090555 A1 | 4/2009 | Boone et al. |
| 2009/0159294 A1 | 6/2009 | Abdollahi et al. |
| 2009/0225630 A1 | 9/2009 | Zheng et al. |
| 2009/0259446 A1 | 10/2009 | Zhang et al. |
| 2010/0114493 A1 | 5/2010 | Vestal |
| 2010/0328095 A1 | 12/2010 | Hawthorn et al. |
| 2011/0180107 A1 | 7/2011 | Dahl |
| 2011/0214882 A1 | 9/2011 | Santos |
| 2011/0220410 A1 | 9/2011 | Aldred et al. |
| 2011/0280104 A1 | 11/2011 | McClung, III |
| 2011/0308332 A1 | 12/2011 | Blessum et al. |
| 2012/0059521 A1 | 3/2012 | Iversen et al. |
| 2012/0123756 A1 | 5/2012 | Wang et al. |
| 2012/0163932 A1 | 6/2012 | Schmidt et al. |
| 2012/0188090 A1 | 7/2012 | Wessling et al. |
| 2012/0222854 A1 | 9/2012 | McClung |
| 2012/0242822 A1 | 9/2012 | Rodney et al. |
| 2012/0267168 A1 | 10/2012 | Grubb et al. |
| 2013/0013100 A1 | 1/2013 | Dahl |
| 2013/0073207 A1 | 3/2013 | Ganz |
| 2013/0076907 A1 | 3/2013 | Hobbs et al. |
| 2013/0236064 A1 | 9/2013 | Li et al. |
| 2013/0265409 A1 | 10/2013 | Tjhang et al. |
| 2013/0275100 A1 | 10/2013 | Ellis et al. |
| 2013/0345878 A1 | 12/2013 | Austefjord et al. |
| 2014/0002617 A1 | 1/2014 | Zhang et al. |
| 2014/0020954 A1 | 1/2014 | Pelletier et al. |
| 2014/0046628 A1 | 2/2014 | Ligneul et al. |
| 2014/0138323 A1 | 5/2014 | Jones et al. |
| 2014/0192253 A1 | 7/2014 | Laroia |
| 2014/0214325 A1 | 7/2014 | Wessling et al. |
| 2014/0326505 A1 | 11/2014 | Davis et al. |
| 2014/0333754 A1 | 11/2014 | Graves et al. |
| 2015/0009325 A1 | 1/2015 | Kardashov |
| 2015/0013448 A1 | 1/2015 | Smith |
| 2015/0114634 A1 | 4/2015 | Limbacher |
| 2015/0138337 A1 | 5/2015 | Tjhang et al. |
| 2015/0218936 A1 | 8/2015 | Maher et al. |
| 2015/0345261 A1 | 12/2015 | Kruspe et al. |
| 2016/0090799 A1 | 3/2016 | Geehan et al. |
| 2017/0089153 A1 | 3/2017 | Teodorescu |
| 2017/0138171 A1 | 5/2017 | Richards et al. |
| 2017/0145807 A1 | 5/2017 | Wendorf et al. |
| 2017/0152729 A1 | 6/2017 | Gleitman et al. |
| 2017/0161885 A1 | 6/2017 | Parmeshwar et al. |
| 2017/0167853 A1 | 6/2017 | Zheng et al. |
| 2017/0284184 A1 | 10/2017 | Anghelescu et al. |
| 2017/0322086 A1 | 11/2017 | Luharuka et al. |
| 2018/0003026 A1 | 1/2018 | Boone et al. |
| 2018/0171731 A1 | 6/2018 | Bingham et al. |
| 2018/0180524 A1 | 6/2018 | Francois et al. |
| 2019/0100988 A1 | 4/2019 | Ellis et al. |
| 2019/0102612 A1 | 4/2019 | Takemoto et al. |
| 2019/0136650 A1 | 5/2019 | Zheng et al. |
| 2019/0141294 A1 | 5/2019 | Thorn et al. |
| 2019/0206068 A1 | 7/2019 | Stark et al. |

FOREIGN PATENT DOCUMENTS

| | | | |
|---|---|---|---|
| JP | 2001101928 A | 4/2001 | |
| JP | 2004285275 A | 10/2004 | |
| JP | 2011207973 A | 10/2011 | |
| JP | 5725347 B2 | 4/2015 | |
| JP | 2015143299 A | 8/2015 | |
| WO | WO-2013089683 A1 * | 6/2013 | ............ E21B 44/00 |
| WO | 2013105930 A1 | 7/2013 | |
| WO | 2015002653 A1 | 1/2015 | |
| WO | 2016077521 A1 | 5/2016 | |
| WO | 2016147045 A1 | 9/2016 | |
| WO | 2017042677 A1 | 3/2017 | |
| WO | 2017132297 A2 | 8/2017 | |
| WO | 2017176689 A1 | 10/2017 | |
| WO | 2018067122 A1 | 4/2018 | |
| WO | 2018093273 A1 | 5/2018 | |
| WO | 2018131485 A1 | 7/2018 | |
| WO | 2018148832 A1 | 8/2018 | |
| WO | 2018157513 A1 | 9/2018 | |

OTHER PUBLICATIONS

U.S. Appl. No. 14/938,962, "Final Office Action", Jul. 16, 2019, 12 pages.

(56) References Cited

OTHER PUBLICATIONS

U.S. Appl. No. 14/938,962, "Non-Final Office Action", Nov. 16, 2017, 10 pages.
U.S. Appl. No. 14/938,962, "Non-Final Office Action", Dec. 31, 2018, 12 pages.
U.S. Appl. No. 14/938,962, "Notice of Allowance", Oct. 24, 2019, 8 pages.
U.S. Appl. No. 16/749,588, "Final Office Action", Jun. 7, 2021, 8 pages.
U.S. Appl. No. 16/749,588, "Non-Final Office Action", Nov. 15, 2021, 10 pages.
U.S. Appl. No. 16/749,588, "Non-Final Office Action", Apr. 1, 2021, 8 pages.
U.S. Appl. No. 16/749,588, "Notice of Allowance", Mar. 17, 2022, 8 pages.
U.S. Appl. No. 17/808,986, "Advisory Action", Jul. 31, 2023, 7 pages.
U.S. Appl. No. 17/808,986, "Final Office Action", Apr. 4, 2023, 14 pages.
U.S. Appl. No. 17/808,986, "Non Final Office Action", Sep. 13, 2023, 8 pages.
U.S. Appl. No. 17/808,986, "Non-Final Office Action", Sep. 28, 2022, 13 pages.
U.S. Appl. No. 17/808,986, "Notice of Allowance", Apr. 9, 2024, 6 pages.
CA2,967,774, "Notice of Allowance", Dec. 16, 2022, 1 page.
CA2,967,774, "Office Action", Feb. 10, 2022, 3 pages.
Guilherme et al., "Petroleum Well Drilling Monitoring Through Cutting Image Analysis and Artificial Intelligence Techniques", Engineering Applications of Artificial Intelligence, vol. 24, No. 1, Feb. 2011, pp. 201-207.
Karimi, "Drill-Cuttings Analysis for Real-Time Problem Diagnosis and Drilling Performance Optimization", SPE Asia Pacific Oil and Gas Conference and Exhibition, Oct. 2013, pp. 1-11.
Marana et al., "An Intelligent System for Petroleum Well Drilling Cutting Analysis", International Conference on Adaptive and Intelligent Systems, Sep. 2009, pp. 37-42.
PCT/US2015/060174, "International Search Report and Written Opinion", Jan. 27, 2016, 7 pages.
PCT/US2015/060186, "International Search Report and Written Opinion", Jan. 29, 2016, 7 pages.
PCT/US2015/060272, "International Search Report and Written Opinion", Jan. 14, 2016, 8 pages.
PCT/US2015/060318, "International Search Report and Written Opinion", Jan. 28, 2016, 8 pages.
PCT/US2016/049704, "International Search Report and Written Opinion", Nov. 10, 2016, 10 pages.
PCT/US2016/049714, "International Search Report and Written Opinion", Nov. 18, 2016, 9 pages.

* cited by examiner

SYSTEM AND METHOD FOR MEASURING CHARACTERISTICS OF CUTTINGS FROM DRILLING OPERATIONS WITH COMPUTER VISION

CROSS-REFERENCES TO RELATED APPLICATIONS

This application is a continuation of and claims the benefit of priority of U.S. patent application Ser. No. 17/808,986, filed on Jun. 25, 2022 entitled SYSTEM AND METHOD FOR MEASURING CHARACTERISTICS OF CUTTINGS FROM DRILLING OPERATIONS WITH COMPUTER VISION, which is a continuation of and claims the benefit of priority of U.S. patent application Ser. No. 16/749,588, filed on Jan. 22, 2020 entitled SYSTEM AND METHOD FOR MEASURING CHARACTERISTICS OF CUTTINGS FROM DRILLING OPERATIONS WITH COMPUTER VISION, now U.S. Pat. No. 11,408,266, issued Aug. 9, 2022, which is a continuation of and claims the benefit of priority of U.S. patent application Ser. No. 14/938,962 filed on Nov. 12, 2015 entitled SYSTEM AND METHOD FOR MEASURING CHARACTERISTICS OF CUTTINGS AND FLUID FRONT LOCATION DURING DRILLING OPERATIONS WITH COMPUTER VISION, now U.S. Pat. No. 10,577,912, issued Mar. 3, 2020, which in turn claims benefit of priority of U.S. Provisional Patent Application No. 62/078,573 filed Nov. 12, 2014, entitled SYSTEM AND METHOD FOR MEASURING CHARACTERISTICS OF CUTTINGS DURING DRILLING OPERATIONS WITH COMPUTER VISION, U.S. Provisional Patent Application Ser. No. 62/212,233 filed Aug. 31, 2015, entitled SYSTEM AND METHOD FOR MEASURING FLUID FRONT POSITION ON SHALE SHAKERS, and U.S. Provisional Patent Application Ser. No. 62/212,252 filed Aug. 31, 2015, entitled SYSTEM AND METHOD FOR ESTIMATING CUTTING VOLUMES ON SHALE SHAKERS. The specifications of all the foregoing applications and patents are hereby incorporated by reference in their entirety as fully set forth herein and for all purposes.

FIELD OF THE INVENTION

The invention relates to systems and methods for measuring characteristics and volume of cuttings during drilling operations and locating the fluid front on a shale shaker with computer vision.

BACKGROUND OF THE INVENTION

Modern drilling involves scores of people and multiple inter-connecting activities. Obtaining real-time information about ongoing operations is of paramount importance for safe, efficient drilling. As a result, modern rigs often have thousands of sensors actively measuring numerous parameters related to rig operation, in addition to information about the down-hole drilling environment.

Despite the multitude of sensors on today's rigs, a significant portion of rig activities and sensing problems remain difficult to measure with classical instrumentation, and person-in-the-loop sensing is often utilized in place of automated sensing.

By applying automated, computer-based video interpretation, continuous, robust, and accurate assessment of many different phenomena can be achieved through pre-existing video data without requiring a person-in-the-loop. Automated interpretation of video data is known as computer vision, and recent advances in computer vision technologies have led to significantly improved performance across a wide range of video-based sensing tasks. Computer vision can be used to improve safety, reduce costs and improve efficiency.

As drilling fluid is pumped into the well-bore and back up, it typically carries with it solid material known as drilling cuttings. These cuttings are typically separated from the drilling fluid on an instrument known as a shale shaker or shaker table. The process of separating the cuttings from the fluid may be difficult to monitor using classical instrumentation due to the violent nature of the shaking process. Currently the volume of cuttings is difficult to measure and typically requires man-power to monitor. Knowledge of the total volume and/or approximate volume of the cuttings coming off the shaker table may improve the efficiency, safety, and/or environmental impact of the drilling process.

Additionally, the location and orientation of the fluid front on the shale shaker is an important parameter to the drilling process that may be difficult to measure accurately. Currently this is somewhat difficult to measure and requires man-power to monitor.

Particulate matter that is returned up the well-bore during drilling also contains a great deal of information about the lithology and/or properties of the subsurface, and can give significant insight into the behavior of the well-bore (e.g., indicating cave-ins, or failure to clean). Current drilling operations require human-in-the-loop analysis of these cuttings; a geologist has to go inspect the cuttings on a conveyor belt or other receptacle down-stream from the shale-shakers. This process is time consuming, expensive, and error prone. Classical instrumentation approaches to particle analysis are extremely difficult to design and implement—the sizes, shapes, and consistencies of cuttings prohibit most automated mechanical handling and measurement. In contrast, significant information can be obtained from visual analysis of the particles on the shaker and this information can be used to make better decisions about proper drilling parameters quickly.

Therefore there is a need for an automated computer vision based technique for identifying cuttings on a belt, and estimating various features regarding their shape, size, volume and other parameters. Information from this system can be used to provide real-time information about the well-bore to the drill-team, flag unexpected changes in the particle sizes and shapes, and/or provide a long-term recording of the particle characteristics for post-drilling analyses.

There is also a need for an automated computer vision based technique for estimating the location of the fluid front on the shale shaker.

This information may also be used to optimize, improve, or adjust the shale-shaker angle (saving mud, and/or increasing efficiency); alert an operator to expected and/or unexpected changes in the cuttings volumes which may, in some cases, be indicative of hole cleaning, influx, losses, and/or other problems; and show whether or not the volume and characteristics of cuttings exiting the shaker is less than, greater than or approximately commensurate with the rate of penetration ("ROP").

BACKGROUND OF THE INVENTION

The present invention, as disclosed and described herein, in one aspect thereof includes a computer vision system for monitoring cuttings from drilling, the computer vision system comprising a camera oriented to face at least a portion of a screen surface of a shaker having drilling mud or cuttings thereon from a well during drilling; a processor coupled to the camera; and a memory coupled to the processor. The memory may comprise instructions executable by the processor to acquire a first plurality of images from the camera; detect a first plurality of particles from the first plurality of images; obtain first particle data associated with the first plurality of images; and model a first distribution of the first plurality of particles based at least in part on the first particle data associated with the first plurality of images. The memory may further comprise instructions executable by the processor to acquire a second plurality of images from the camera; detect a second plurality of particles from the second plurality of images; obtain second particle data associated with the second plurality of images; and model a second distribution of the second plurality of particles based at least in part on the second particle data associated with the second plurality of images. Furthermore, the memory may comprise instructions executable by the processor to determine a difference in a likelihood of a distribution of particles based at least in part on the first distribution and the second distribution; and provide an alert if the difference in the likelihood of the distribution of particles falls outside a threshold range.

In various embodiments, the first plurality of particles and the second plurality of particles each comprise a volume of cuttings per unit of time.

In various embodiments, the instructions are further executable by the processor to initiate, inhibit, or interrupt a drilling activity if the difference in the likelihood of the distribution of particles falls outside the threshold range.

In various embodiments, the first distribution of the first plurality of particles is based at least in part on a density estimate of the first plurality of particles from the first plurality of images.

In various embodiments, the alert comprises a visual alert or a text message regarding the difference in the likelihood of the distribution of particles falling outside the threshold range.

In various embodiments, the instructions are further executable by the processor to obtain historical data associated with a plurality of historical images from the camera acquired during drilling one or more previous wells; and identify one or more drilling conditions from the historical data.

In various embodiments, the instructions are further executable by the processor to determine a drilling condition of the one or more drilling conditions has occurred based at least on the historical data and the difference in the likelihood of the distribution of particles falling outside the threshold range.

In an aspect, a method for monitoring cuttings from drilling can comprise acquiring, by a computer vision system, a plurality of images from a camera oriented to face at least a portion of a screen surface of a shaker having drilling mud or cuttings thereon from a well during drilling; detecting, by the computer vision system, a plurality of particles from the plurality of images; obtaining, by the computer vision system, data associated with the plurality of particles; modeling, by the computer vision system, a statistical distribution of particles based at least in part on the data associated with the plurality of particles; and monitoring, by the computer vision system, the statistical distribution of particles over time. The method can further comprise determining, by the computer vision system, a change in a likelihood of the monitored statistical distribution of particles based at least in part on the modeled statistical distribution of particles; and providing, by the computer vision system, an alert if the change in the likelihood of the monitored statistical distribution of particles falls outside a threshold range.

In various embodiments, the plurality of particles comprises a volume of cuttings per unit of time.

In various embodiments, the method further comprises initiating, inhibiting, or interrupting a drilling activity if the change in the likelihood of the monitored statistical distribution of particles falls outside the threshold range.

In various embodiments, the statistical distribution of particles is based at least in part on a density estimate of the plurality of particles from the plurality of images.

In various embodiments, the alert comprises a visual alert or a text message regarding the change in the likelihood of the monitored statistical distribution of particles falling outside the threshold range.

In various embodiments, the method further comprises obtaining, by the computer vision system, historical data associated with a plurality of historical images from the camera acquired during drilling one or more previous wells; and identifying one or more drilling conditions from the historical data.

In various embodiments, the method further comprises determining a drilling condition of the one or more drilling conditions has occurred based at least in part on the historical data and the change in the likelihood of the monitored statistical distribution of particles falling outside the threshold range.

In an aspect, a non-transitory computer readable storage medium comprising a plurality of instructions executable by one or more processors, the instructions comprising instructions which, when executed on the one or more data processors, cause the one or more data processors to perform actions including acquiring a plurality of images from a camera oriented to face at least a portion of a screen surface of a shaker having drilling mud or cuttings thereon from a well during drilling; detecting a plurality of particles from the plurality of images; obtaining data associated with the plurality of particles; modeling a statistical distribution of particles based at least in part on the data associated with the plurality of particles; and monitoring the statistical distribution of particles over time. The instructions further comprise instructions which, when executed on the one or more data processors, cause the one or more data processors to perform actions including determining a change in a likelihood of the monitored statistical distribution of particles based at least in part on the modeled statistical distribution of particles; and providing an alert if the change in the likelihood of the monitored statistical distribution of particles falls outside a threshold range.

DETAILED DESCRIPTION OF THE INVENTION

Figure 1:
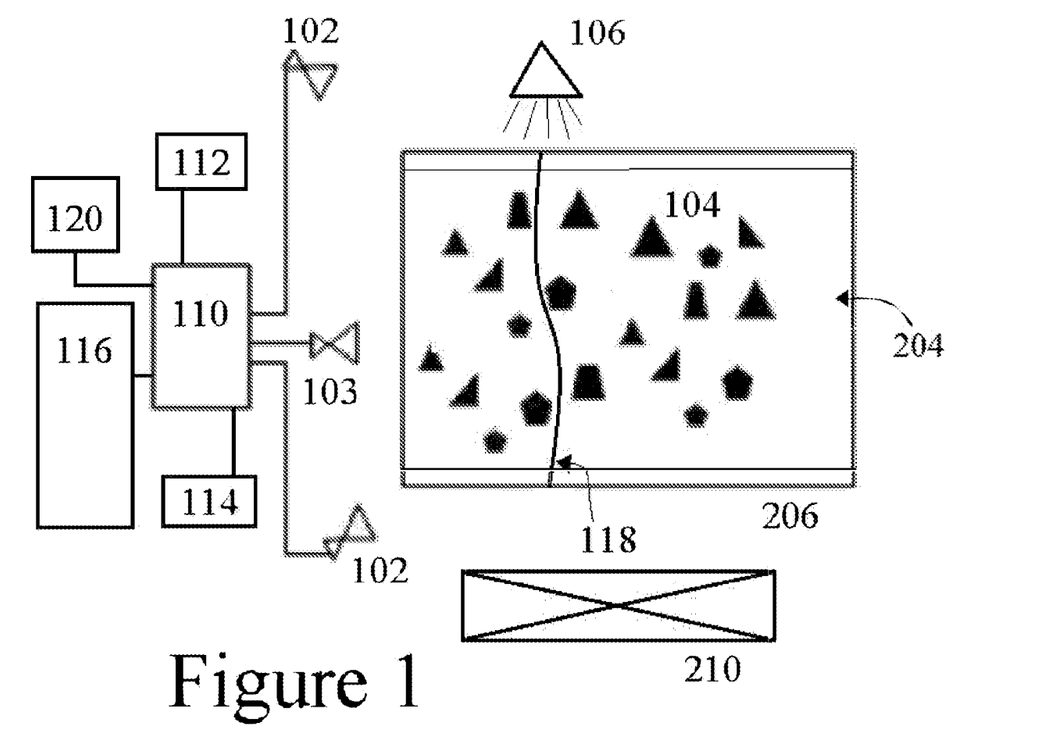
FIG. 1 depicts one of many potential embodiments of a system involving at least one camera and processor for monitoring drilling cuttings.
Figure 2:
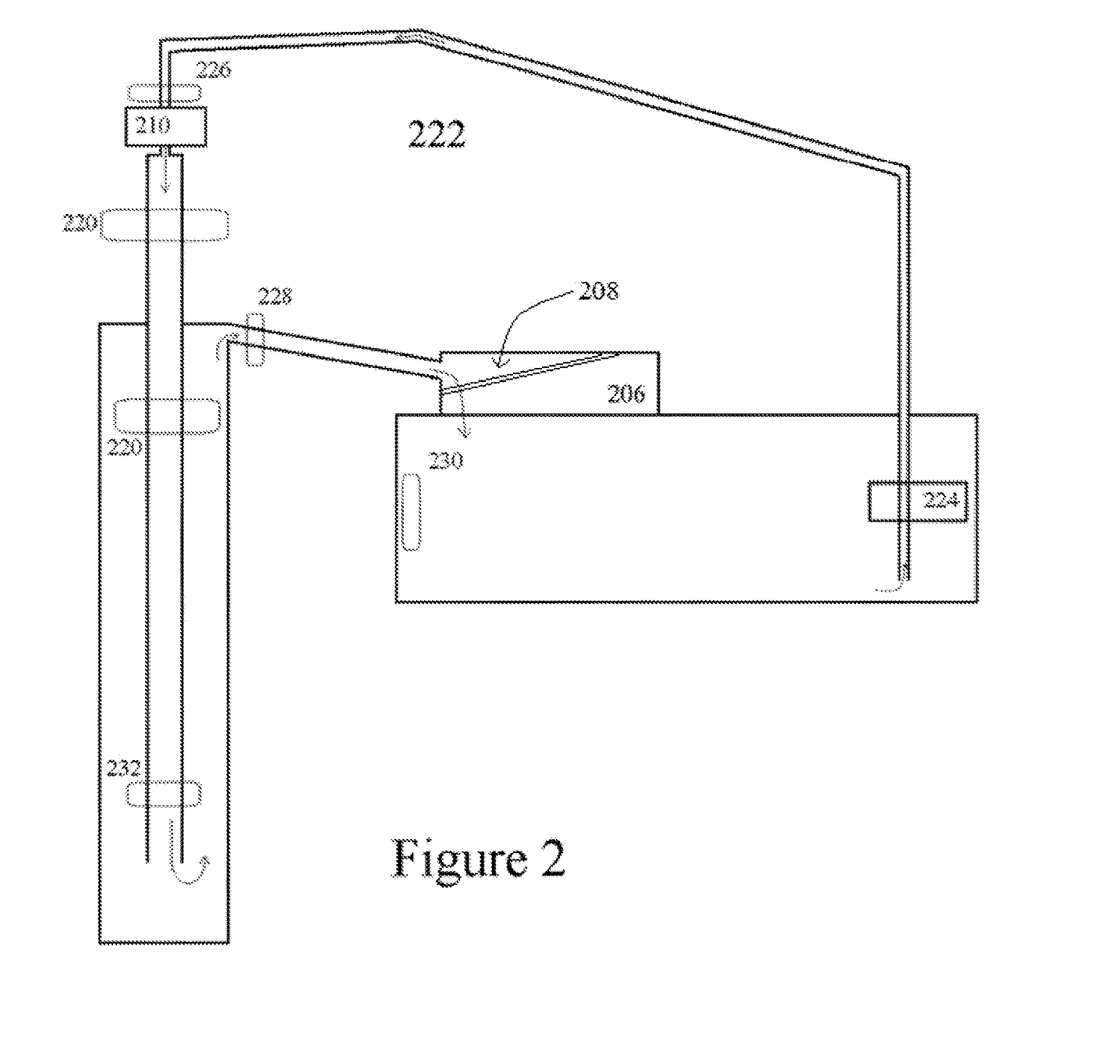
FIG. 2 depicts an embodiment in the context of a simplified well circulatory system and multiple sensors which may assist the system in determining the volume and/or characteristics of drill cuttings.

The disclosed method and system typically contains several parts including at least one camera 102 (video, or single-frame) oriented as to view a shaker table 206 on which the particulate matter passes and/or oriented to view the cuttings 104 as they approach and/or fall off the edge of a shaker table 206. The system and variations of the system may also include a belt 204, shaker table screen 208, machinery control system 116 and other drilling or industrial equipment 210. Cameras 102 may be oriented as to provide off-axis views (e.g., 90 degrees offset), or may be oriented in the same general direction, but spatially offset to provide stereo vision. In alternative embodiments, Red Green Blue-Depth ("RGB-D") cameras, ranging cameras, and/or other distance-sensing technologies 103, such as Light Detection and Ranging ("LIDAR"), may be used in addition to, or in place of cameras 102.

Depending on the speed of the belt 204 and the rate at which particles 104 are moving, cameras may collect frames as slow as 0.003 Hz (1 frame/5 minutes) or much faster. Each camera 102 may comprise or be connected to a computer 110 which performs particle 104 detection and/or extracts one or more features (e.g., statistical descriptors, RGB values, texture features, edge-descriptors, object matching descriptors or bounding boxes) from one or more up to each detected particle 104.

Information about these particles 104 may be accumulated on a central computing resource 110. In the case of multiple cameras 102, information about the camera's 102 relative pose and orientation, and the corresponding particle 104 bounding boxes may be used to combine information about particles 104 that may be visible in both cameras 102. The resulting information about particles 104 may then be tracked over time and logged to a database 112 for later retrieval and further analysis. Alternatively, this information may be tracked over time and changes in the statistical distributions of the particles 104 may be flagged and brought to the mud-logger's or drill-team's attention with, for example, a plain-text description of the observed change (e.g., "the average cutting size has increased by 20% in the last 3 minutes"), and the corresponding video data. This information could also be used in a supervised classification system, trained using prior data to identify specific discrete cases—e.g., "cutting is from a cave-in", or "cutting is due to X". Supervised classification may be used on each particle 104 independently, or on the statistics of the particles 104 in the current frame and recent time in aggregate. Outputs from the classification system may be presented to the mud-logger's or drill-team's attention with, for example, a plain-text description of the observed change (e.g., "cuttings indicative of cave-in detected"), and the corresponding video data.

Each camera 102 may comprise, or may be connected to, a processor 110 which may be configured to perform detection and localization of the drilling cuttings 104 on the shaker 206. The processor 110 may additionally or alternatively be configured to identify cuttings 104, track the cuttings 104, and/or estimate the volume of cuttings 104 coming off the end of a shaker 206. These actions may also be performed on a per unit time basis when desirable. In some embodiments, information from a camera 102 may be combined with information from multiple other sensors 220. Information related to the flow-in, drilling pumps, flow-out, and/or pit volume, collectively known as the circulation system 222, may be useful in combination with some embodiments. By combining this information, the system may be able to provide different information and/or alerts under different conditions, such as when the pumps are on vs. off. Information across the different sensor 220 modalities may be fused to allow the system to make better decisions under certain circumstances.

Disclosed embodiments include many possible combinations of cameras 102, distance-sensing equipment 103 and sensors 220. For example, optical or video cameras 102, single or multi-stereo-cameras 102, night-vision cameras 102, IR, LIDAR, RGB-D cameras, or other recording and/or distance-sensing equipment 103 may all be used, either alone or in combination. Each camera 102 or combination of cameras 102 and sensors 220 may be used to track the volume or other characteristics of cuttings 104 on or exiting a shaker 206. Information from the cameras 102 and/or sensors 220 may be combined with information from the circulation system 222 (e.g., flow-in, flow-out, and pit-volume) to modify the system's behavior as desired.

Information about the absolute and/or relative change in cutting 104 volumes or other characteristics of cuttings 104 coming off of the shaker table 206 may, under certain conditions, be combined with circulation system 222 parameters and/or other drilling parameters, such as rate of penetration, and be relayed to the drilling engineer or other personnel. For example, a sudden change, either decreases or increases, in the cuttings 104 volume not correlated to changing rate of penetration may indicate hole cleaning problems, influxes, and/or other changes in conditions. Additionally, a sudden change in the spatial characteristics of the cuttings 104 may indicate a cave-in or other phenomena.

Cameras 102 (optical, IR, RGB-D, single, stereo, or multi-stereo among others) may be mounted within pre-defined constraints around the shaker table 206. In an embodiment, camera 102 orientations are approximately 45 degrees to the shaker table 206, but cameras 102 may be placed anywhere with a view of the cuttings 104 and/or the fluid front 118. This may include from 0 to 180 degrees pitch. When using a single camera 102, it may be preferable to place the camera 102 within a range of 60 degrees to −60 degrees of vertical. The camera 102 may be configured to capture a view from above, oriented approximately down at the top of the shaker 206.

In some embodiments, multiple cameras 102 may be placed in mutually beneficial locations. As an example, stereo vision approaches may improve particle 104 size estimation. Stereo cameras 102 typically view the same scene from approximately the same angle but from different spatial locations. Alternatively, cameras 102 viewing the same scene from different angles, such as a front view, side angle view, and/or overhead view may provide different views of the same objects and may reduce the need for assumptions, such as rotational symmetry, in volume or other characteristic estimation. Additionally, when using multiple cameras 102, the preferred placement may be a function of the shape and/or size of the shaker 206, the desired volume or characteristic fidelity, and/or the configuration of sensors 220 under consideration. Preferably, multiple camera 102 placements may be configured to provide additional information from each camera 102 or sensor 220 as discussed.

Cameras 102 may be equipped with a flash or other light source 106 to maintain substantially adequate illumination across multiple images. This may be useful since the ambient lighting can change significantly depending on the time of day or night and/or the weather conditions. By maintaining adequate lighting, some processing complications may be able to be avoided.

In some embodiments, cameras 102 and/or distance-sensing equipment 103 may be configured to move in response to pre-determined criteria. This movement may comprise rotation, panning, tilting and/or zoom adjustments along any axis. The movement may be automated or may be performed by staff. These adjustments may be predicated on conditions including but not limited to observed features or characteristics of the cuttings, environmental conditions surrounding the rig and/or shale shaker and/or input from other sensors.

Different behaviors of the cuttings 104 and shakers 206 may be expected during active-flow periods when the mud pumps 224 are running and passive periods when the mud pumps 224 are off. Additional changes may manifest during the transient periods shortly after the pumps 224 switch either on or off. Additional data about the drilling process, such as hook load, bit depth, or rate of penetration, among others, may also be used to provide contextual information to the computer vision system in certain conditions.

In some embodiments, discrete cuttings 104 may be identified on or near the shaker 206, and/or as they fall off the end of the shaker 206 using one of many image processing features and techniques. Background subtraction and/or change detection may be used to identify cuttings 104 in part because cuttings may appear different than the typical background, which may consist of a shale shaker 206, shale shaker screen 208, and/or other background features. Cuttings 104 may also appear different from the typical background when falling off the edge of the shaker 206. Cuttings may additionally appear to "move" at an approximately constant velocity across a shaker table 206. These features may enable background estimation and/or subtraction techniques to be used to identify individual cuttings 104. Texture features may also be used for detection of drilling cuttings 104. Cuttings 104 may have an image texture which is different from the background. This may allow the cuttings 104 to be detected using this difference in texture. This detection may be accomplished using one-class classifiers to distinguish cuttings 104 as differences from the background and/or vice-versa. Two-class classifiers may also be used to actively distinguish two classes, one class for cuttings 104 and another for background. It will be appreciated that multiple-class classifiers may also be used when desirable.

In other embodiments, reflectivity and/or color properties may also be used for cutting 104 detection. Cuttings 104 may often be covered in drilling fluid and therefore may have different reflectivity and/or coloration than the background (shale shaker 206, conveyor belt 204, and/or other background features). Cuttings 104 may therefore be detectable using these changes in color and reflectivity. It will be noted that these techniques may also be applicable when the cuttings 104 are not covered in drilling fluid, as long as the cuttings 104 do not present the same reflectivity and color characteristics as the background.

Alternative embodiments may additionally and/or alternatively use persistence and/or tracking techniques to identify cuttings 104. Cuttings 104 often maintain approximately constant shape and size as they travel across the shaker 206. As a result, individual cuttings 104 may be able to be tracked and/or disambiguated across multiple frames. Tracking cuttings 104 may be accomplished using any of a number of tracking techniques, (e.g., Kalman filters, particle filters, and/or other ad-hoc tracking techniques). This may enable resolution of the cuttings 104 as multiple "looks" are aggregated on each cutting 104. In some embodiments, this may enable more accurate volume or characteristic estimation as well.

Still more embodiments may use fluid and/or cuttings 104 velocity estimation to identify cuttings 104. Cuttings 104 often move across the shaker screen 208 at approximately the same velocity as one another. This velocity may be estimated across all of the observed cuttings 104 and/or be tracked (e.g., with a Kalman filter or particle filters). This information may then be used to identify other cuttings 104 and/or predict the eventual locations of cuttings 104 that may be temporarily lost during the tracking and identification stage. Changes in this velocity may also be flagged to an operator.

In embodiments that comprise multiple cameras 102, LIDAR, RGB-D cameras and/or other distance sensing equipment 103, particles 104 may be identified using the observed "height" of the cuttings 104 as compared to the expected background height.

Techniques similar to those discussed may also be applicable in hyperspectral, IR, or other imaging modalities. As cuttings 104 are tracked on the shaker 206, conveyor belt 204, and/or other devices, their volume and characteristics can be estimated in several ways. In embodiments using single-sensor RGB cameras 102 or similar devices, the approximate volume of cuttings 104 may be estimated from a single viewpoint using rotationally symmetric assumptions about the cuttings 104, and the known, calculated, and/or estimated camera-to-shaker table distance. Alternatively, a cutting 104 shape inference may be made using knowledge of the available light source and estimating the reflectivity as a function of space on the visible parts of the cutting 104.

For embodiments using single-sensor RGB cameras 102 or similar devices, the approximate volume of the cuttings 104 may also be estimated using previously trained regression techniques which determine the approximate object volume using image region features (e.g., eccentricity, perimeter length, and area among others) extracted from individual cuttings 104 in the image. These image region features may be used to identify changes in the cutting 104 shapes as well.

Embodiments which use multiple cameras 102, combined camera 102 (e.g., stereo-camera) scenarios, or distance detection sensors 103, depth-information may be directly available and/or inferable. This may provide the visible cross-section of the object and/or a measure of how that cross-section varies with height. This information may be used to improve the volume estimation by reducing the symmetry assumptions required to estimate the volume of each cutting 104.

In some embodiments, the total volume of all the cuttings 104 visible in a scene, image, and/or frame may be estimated by combining information from the detection, tracking, and/or volume estimation portions of the techniques discussed. In other embodiments, the net volume flow may be calculated by considering the amount of volume entering or exiting the visible region per unit time. Alternatively, the change in volume may be estimated by calculating the volume of particles 104 passing by a specified "line" in real-world space (e.g., the end of the shaker 206), or through a specified region on the shaker 206 or in the background. Depending on the particular installation, camera 102 availability, and/or configuration, the total volume estimation may be appropriate for actual volume estimation in real-world units (e.g., 1 $m^3$ of cuttings 104 per 5 minutes), and/or in relative terms (e.g., a 5% increase in cuttings 104 volume in the last 5 minutes). Both may be valuable metrics in certain circumstances, but real-world units are preferable as the percent change can be derived from this information.

In still more alternative embodiments, information from the camera(s) 102 may be combined with information from the circulation system 222 (e.g., flow-in, flow-out, ROP, and/or pit-volume) or other rig sensors 220 to change the detection system behavior. As discussed, information across the different sensor 220 modalities may be fused to make better decisions. As drilling continues, the camera 102 system may be able to auto-calibrate to determine what a realistic amount of cuttings 104 per meter drilled is (e.g., leveraging ROP), and may additionally use this for automatic alarming if the observed volume of cuttings differs or diverges significantly. In addition to activating an alarm 114, the system may initiate, alter, interrupt, or inhibit automated activity by equipment 210 connected to the system.

Information regarding sudden unexpected changes in the volume, shapes, velocities, and or other characteristics of the cuttings 104 can be brought to the user's attention visually, audibly, or with other notifications. These notifications may be complete with photographs of the current situation and/or a plain-text description of the cause of the alarm (e.g., "sudden increase in volume of cuttings").

In other embodiments, the video data and/or other data may also be tagged along with any information extracted during the computer vision processing process. Gathered information may be displayed to an operator with a user interface which may include an annotated image of the shaker tables 206 under consideration. This image may be automatically annotated and may also, in certain embodiments, display marks identifying a variety of key features, such as the fluid front 118, cuttings 104, any potential issues, etc.

In another embodiment, the volume of cuttings 104 on or coming off the shaker table 206 may be estimated using a two-step process of particle 104 detection followed by volume estimation. The use of RGB and IR cameras 102 may be useful under certain circumstances. Particle 104 detection can be accomplished using any of a number of image processing techniques, including but not limited to corner detection, blob detection, edge detection, background subtraction, motion detection, direct object detection, adaptive modeling, statistical descriptors and a variety of similar techniques. The proper particle 104 detection approach may be site-dependent, based on the local lithology. Object detection may also be obtained using standard background depth estimation and/or subtraction approaches. The use of distancing equipment 103, such as LIDAR and/or RGB-D cameras, may have advantages with regard to these techniques.

Once a cutting 104 has been detected, a camera 102 may be used to estimate cutting 104 volumes or other characteristics using the known camera 102 transform parameters, the known distance to the shaker 206, and/or the shape and/or size of the detected object as it appears in the camera 102 frame. Similar processing is applicable for many types of cameras 102, such as RGB, and IR cameras 102. For multiple cameras 102 viewing the same scene, stereo vision techniques may be used to obtain a potentially more detailed 3-D representation of the cuttings 104, and thereby achieve more accurate volume estimations. If RGB-D or LIDAR 103 data is available, these may be used to render 3-D models of the cuttings 104, for higher fidelity volume estimation.

Given the particle's 104 bounding boxes, various features about each detected particle 104 may then be extracted. These include various object shape parameters (e.g., image moments), texture features, HOG features, color descriptors, integral channel features, or the raw pixel data.

Information about particles 104 may be aggregated both temporally and spatially. Spatial information can be accumulated across multiple cameras 102 by using information about each individual camera's 102 pose to infer when detections in the two cameras 102 correspond to the same cutting 104. Similarly, information can also be aggregated temporally when the camera 102 frame-rate is fast enough to capture multiple images of the same object as it passes down the belt 204 in the same camera 102.

After aggregation, one or more up to each unique detected particle 104, but typically a representative sample size, is associated with a corresponding feature vector (an accumulation of the image moments, RGB values, HOG features, etc.). These features can be used to perform inference, track statistics, and perform classification as discussed below. In some embodiments, all or most of the available particles 104 will be detected by the system, while many other embodiments will detect a significant percentage, but not 100% of all particles 104. Certain disclosed embodiments may be able to function as described with a very small but representative sampling of the total number of available particles 104. A representative sample may be as few as 0.1% of all available particles 104. Alternatively a representative sample may be greater than 1%, greater than 10%, greater than 25%, greater than 50%, greater than 75%, greater than 90% or greater than 95% of the total particles 104 available.

The information about each cutting 104 as it passes through the camera 102 field-of-view, along with the complete image data, cutting 104 bounding boxes, associated features, and meta-data (e.g., time, rig identifier, weather information, drill bit depth, etc.) may be recorded to a database 112 which can be leveraged post-hoc and combined with databases 112 from other drilling experiments.

The statistical distribution of the cuttings 104 may be tracked as a function of time. This may be accomplished using either parametric (e.g., Gaussian distributions) or non-parametric Bayesian models (e.g., Dirichlet process mixtures) or using adaptive histograms, where the current density, p(x, f), is estimated using:

$$p(x, f) \propto \frac{\tau h(x, f)}{N_t} + (1 - \tau) p(x, f - 1)$$

Where $N_t$ represents the number of cuttings 104 detected in the frame number f, h(x, f) represents the histogram of features (x) from all N cuttings 104 in the current frame, $\tau \in [0,1]$ controls the speed of adaptation, and p(x, f−1) represents the density estimate from the previous frame.

When the likelihood of the current data, x, is very low, e.g., $$p(x, f - 1) < \theta$$

This indicates a sudden change in the distribution of the particles 104, which should be brought to the attention of the mud-loggers or drill-team.

Supervised classification and regression techniques may be utilized to automatically flag any of a number of discrete events that result in changes to the statistics of the cutting 104 features. Supervised techniques rely on a body of previous data from similar scenarios with corresponding labels (e.g., videos of cuttings 104 from cave-in scenarios, videos of cuttings 104 when the well-bore is not being cleaned adequately, etc.). Given this historical data, features may be extracted from the historical video data and supervised techniques (e.g., SVM, RVM, Random Forest, linear discriminant analysis, quadratic discriminant analysis) may be trained to identify these scenarios in new data as it is collected. When new data is collected, the outputs from these supervised classifiers are then presented to the mud-loggers or drill-team as appropriate.

Information regarding sudden changes in the statistical distributions of the cuttings 104, as well as flags raised by the supervised techniques described above may require immediate attention on the part of the mud-loggers or drill-team. Depending on the severity of the type of change encountered, information from the system may be presented to the corresponding person in one of several ways. Information may be entered in the daily automated mud-log (least importance). Information may also be conveyed to appropriate personnel via e-mail, text message, or software-pop-up on the driller's screen, etc. (moderate importance). Alarms 114 or other communications requiring immediate response may also be raised (most importance).

In some cases, alarms 114 may contain a clear text description of the issue discovered (e.g., "The average cutting size increased by 20% in the last 3 minutes"). This alarm 114 may be provided together with a visualization of the camera 102 data prior to the alarm 114, the camera 102 data that caused the alarm 114, diagnostic text, and arrows illustrating the observed changes.

If the processor 110 detects a change in particle 104 characteristics or detects a per-determined condition, the processor 110 may initiate, interrupt, alter or inhibit an automated activity using a machinery control system 116. The machinery control system 116 may increase or decrease the speed of a belt 204. The machinery control system 116 may adjust the tilt of a shale shaker 206 or may make adjustments to the functioning of any other piece of equipment 210. Equipment 210 may include but is not limited to all forms of shake shakers 206, shaker screens 208, drill bits, drilling motors, top drives, pipe elevators, mud pumps 224, valves, and a wide array of other drilling and industrial equipment.

Various control mechanisms may be appropriate to automate the angle and/or position of the shale shaker 206. For example, PID controllers and/or other systems may be used to adjust the shaker 206 based on acquired data. These adjustments may be done automatically, via a closed-loop system, or by instructing an operator to make the necessary changes based on the acquired data.

The cameras 102, distance sensing equipment 103 and/or other sensors 220 and techniques discussed above may additionally be used to identify and localize the fluid front 118 on a shaker table 206. The fluid front 118 is typically where the majority of the mud and/or cuttings slurry ends. This may be where the separated shale cuttings 104 begin and/or where the shaker screen 208 is exposed. The information related to the fluid front 118 may be tracked over time and logged to a database 112 for later retrieval and/or further analysis. This information may also be tracked over time and changes in location or behavior of the fluid may be brought to the mud-logger's or drill-team's attention using any suitable technique, such as a plain-text description of the observed change (e.g., "the fluid front appears to be too far forward on the shaker table"). The corresponding video data may also be provided to the drill-team to allow for independent verification of the alert conditions. The fluid front 118 information may also be used in a closed-loop control system to adjust various parameters, such as the angle or speed of the shaker table 206, if desired. Some embodiments of this system may allow the adjustments to be made automatically without human involvement.

Disclosed embodiments include many possible combinations of cameras 102, distance sensing equipment 103 and sensors 220. Each camera 102 or combination of cameras 102 and sensors 220 may also be used to track the location of the fluid front. Information from the cameras 102 and or sensors 220 can be combined with information from the circulation system 222 (e.g., flow-in, flow-out, and pit-volume) to modify the system's behavior as desired.

Different behaviors of the fluid front 118 and/or shakers 206 may be expected during active-flow periods when the mud pumps 224 are running and passive periods when the mud pumps 224 are off. Additional changes may manifest during the transient periods shortly after the pumps 224 switch either on or off. Additional data about the drilling process, such as hook load, bit depth, or rate of penetration, among others, may also be used to provide contextual information to the computer vision system in certain conditions.

In some embodiments, the fluid front 118 may be identified using a computer vision and machine learning system. For example, texture classification may potentially be used to identify the fluid front 118 since the visual "texture" of the mud as the shale-shaker 206 is vibrating is typically different from the visual texture of the shaker table 206 and/or other nearby objects. The visual texture of the splashing, vibrating, and/or moving fluid behind the fluid front 118 stands in contrast to the relatively regular texture of the rest of the shaker 206. As a result, it may be possible to detect the fluid front 118 using texture features. These features may be used to distinguish an area from the shaker table 206 and/or background features, (e.g., since the distinguished area differs from the shaker 206 and/or background), and/or used in a multi-class classification framework (e.g., a 2-class support vector machine ("SVM")) to distinguish the "shaker" and/or "background" class from the "fluid" class.

Another example of computer vision that may be used to identify the fluid front 118 is change detection. The shale shaker 206 itself may provide a relatively static background. Even when the shaker 206 is moving, the information related to the pixels viewing the shaker 206 may remain stationary. In some embodiments, the information related to the pixels may include the statistical distribution of the pixel intensities in any color space (e.g., RGB). This may allow long-term background estimation (e.g., via Gaussian Mixture Models, robust principal component analysis, etc.) to be used to estimate the background class when the pumps 224 are off and/or shortly after the pumps 224 turn on and before fluid appears on the shaker 206. This technique may also be used when the pumps 224 are on under certain conditions. These models may also be used to flag changes, which may be caused by the advent of the fluid front on the shaker 206.

An additional example of computer vision that may be used to identify the fluid front 118 is reflectivity and/or color detection. The fluid front 118 is often a different color than the shale shaker 206 and may have different reflectance characteristics as well. Reflectance and/or color features may be used for fluid and/or shaker classification on their own, in combination with each other, and/or in combination with other disclosed techniques. Additionally, numerous other descriptor vectors may also be used in conjunction with and/or in addition to the techniques disclosed above. Other possible techniques include, but are not limited to, histogram of oriented gradients ("HOG"), scale invariant feature transform ("SIFT"), speeded-up-robust-features ("SURF"), binary robust independent elementary features ("BRIEF"), Viola-Jones, ("V-J"), Harr wavelet, (deep) convolutional neural networks (CNNs) and others.

Detection of the actual fluid front 118, as compared to the other fluid regions may be accomplished by classifying regions of the image as "fluid," "non-fluid," or any other classifier, and/or using image region properties on the resulting image regions to determine a potential class separating line. The fluid front 118 may be specified as a line, as a more complicated smoothly varying function (e.g., spline, quadratic, etc.), and/or as a combination of any of these. Preferably, the front should be constrained to be on the shale shaker 206.

In some alternative embodiments, the image may be separated into fluid and/or non-fluid regions by hypothesizing numerous locations for the fluid front 118 and choosing at least one location corresponding to a location above a certain threshold likelihood separation between two distributions, one representing the fluid and one representing the shaker. Preferably, a chosen location corresponds to the maximum likelihood separation between the two distributions.

Still other optimization techniques may also be used to identify the location of the fluid front 118. For example purposes only, genetic algorithms, Markov-chain montecarlo ("MCMC") techniques, additional background subtraction and/or correction techniques, among many other techniques may all be used.

Once detected, the fluid front 118 location (line, quadratic, spline formulation, and/or any other demarcation) may be tracked over time. This may be accomplished through many different techniques. For example purposes only, tracking the fluid front 118 over time may be accomplished by appropriately parameterizing the fluid front 118 representation and leveraging time-sensitive Kalman or Particle Filtering approaches to update the location of the fluid front 118 in a frame. Preferably this would be done in many frames, and most preferably in every frame. Alternatively, the fluid front 118 location may be re-estimated in one, some, and/or all frames. This may also be done when the fluid front 118 was not previously detected.

In some embodiments, the fluid front 118 location may be logged to a database 112 for later retrieval and further analysis. Changes in the location or behavior of the fluid may be brought to the mud-logger's or drill-team's attention with a plain-text description of the observed change (e.g., "the fluid front appears to be too far forward on the shaker table"), and the corresponding video data.

In other embodiments, the video data and/or other data may also be tagged along with any information extracted during the computer vision processing process. Gathered information may be displayed to an operator with a user interface which may include an annotated image of the shaker tables 206 under consideration. This image may be automatically annotated and may also, in certain embodiments, display marks identifying a variety of key features, such as the fluid front 118, cuttings 104, any potential issues, etc.

Various control mechanisms may be appropriate to adjust and/or automate the angle and/or position of the shale shaker 206. For example, PID controllers, hydraulic pistons, electronic motors, and/or other systems may be used to adjust the shaker 206 based on acquired data.

The fluid-front 118 location estimation may also be used in a closed-loop control system to adjust various parameters (e.g., the angle) of the shaker table 206. This may enable automatic control of a shaker table 206 system on a rig. This may result in saving time, saving money, and/or preventing undesirable ecological impacts.

FIG. 1 depicts one of many preferred embodiments of the system. Cuttings 104 on a shaker 206 pass through the fluid front 118 and may be illuminated by a light source 106. Cameras 102 and distance sensing equipment 103 are configured to gather data related to the characteristics of the cuttings 104. The cameras 102 and distance sensing equipment 103 are connected to a processor 110 which is operably connected to a database 112, alarm 114 and a machinery control system 116. The machinery control system 116 is configured to initiate, interrupt or inhibit automated activity by equipment 210. The processor 110 may also be connected to a display 120 in order to provide information to an operator.

FIG. 2 depicts a very simplified oil well circulation system 222 which may contain many sensors 220 in addition to mud pumps 224 and drilling equipment 210. It will be appreciated that the specific configuration of the well circulation system 222, sensors 220, mud pumps 224 and drilling equipment 210 may be very different in alternate embodiments disclosed herein. Shale shaker 206 is generally in the path of drilling mud circulation and may be used to screen out cuttings 104 for analysis as well as to preserve drilling mud.

Figure 3:
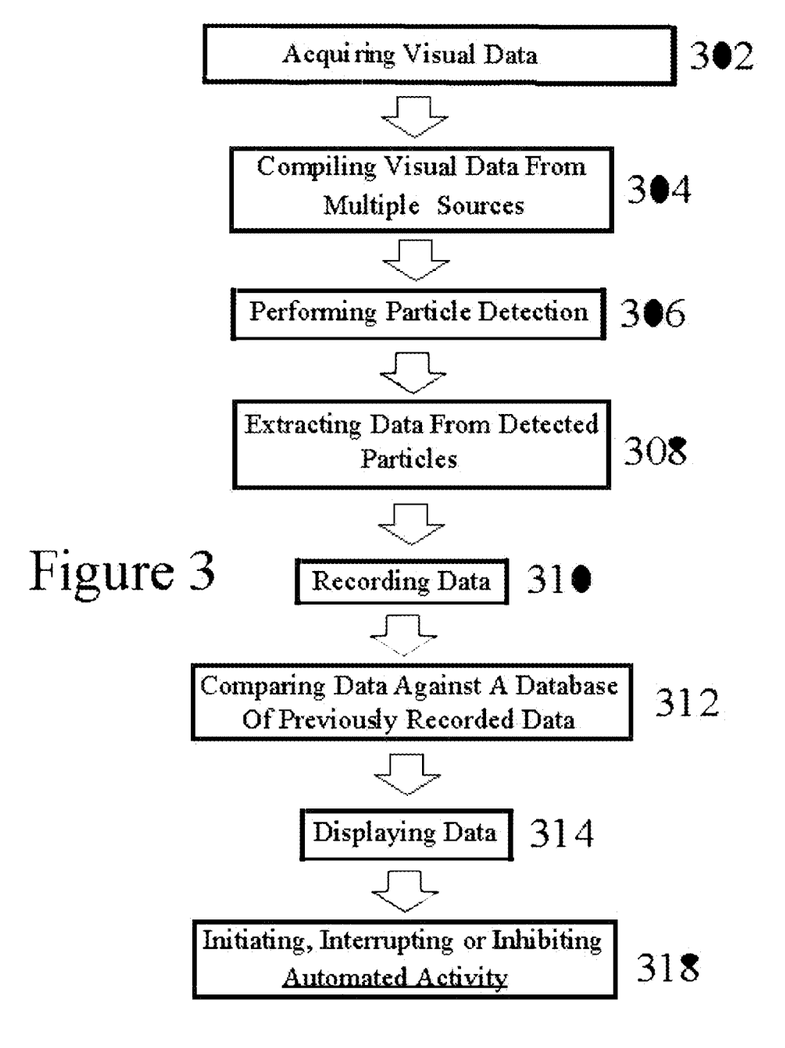
FIG. 3 depicts a block diagram showing the steps of a potential method for measuring the characteristics of drill cuttings.

FIG. 3 shows a block diagram of the steps for a certain method of measuring the characteristics of drill cuttings. The disclosed steps may be organized in a different manner. In certain embodiments one or more of the steps may be removed or exchanged.

Figure 4:
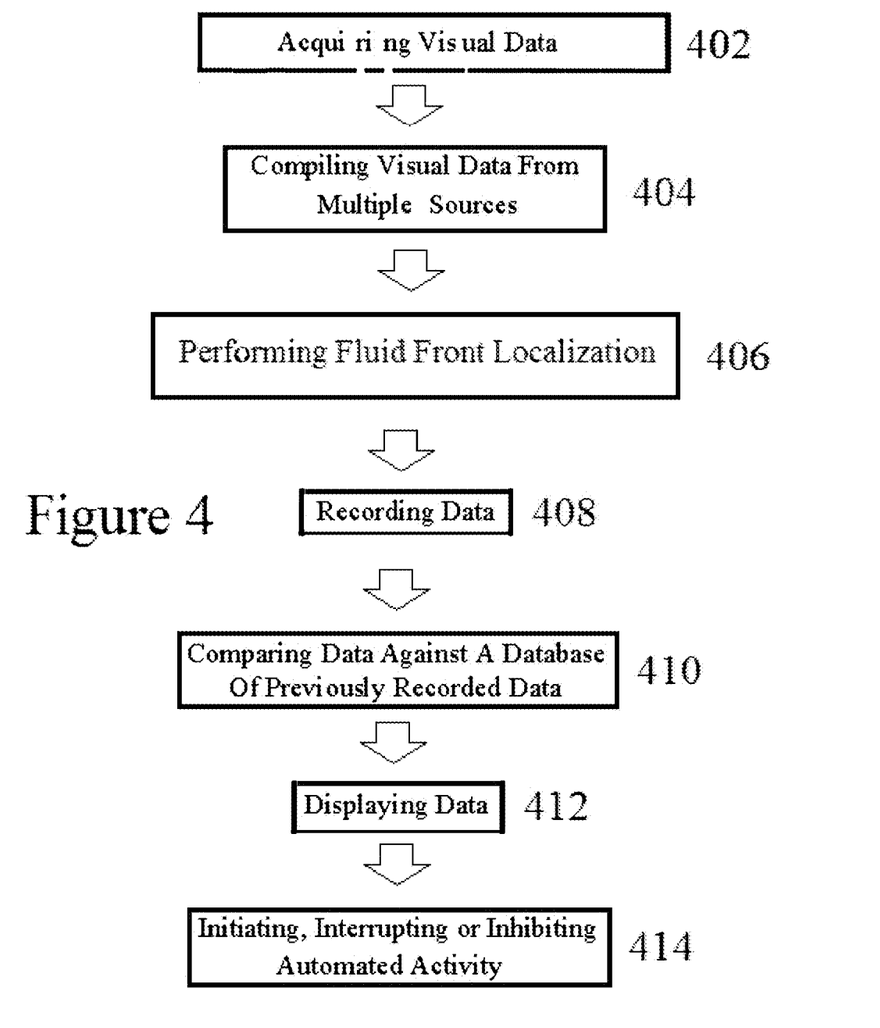
FIG. 4 depicts a block diagram showing the steps of a potential method for localizing a fluid front on a shaker table.

FIG. 4 shows a block diagram of the steps for a certain method of localizing the fluid front 118 on a shaker table 206. The disclosed steps may be organized in a different manner. In certain embodiments one or more of the steps may be removed or exchanged.

Disclosed embodiments relate to a system for monitoring characteristics of drilling cuttings 104 and adjusting automated activity based on the characteristics. The system includes a shaker table 206 which is operably connected to a machinery control system 116. The system also includes at least one camera 102 operably connected to a processor 110. The processor 110 may be configured to perform particle detection, extract features of the particles 104, estimate the volume of the particles 104 using machine vision or a combination of all three steps. The processor 110 is also operably connected to the machinery control system 116 which is configured to adjust automated equipment 210 based on input from the processor 110.

Certain embodiments of the system may also include distance sensing equipment 103 and sensors 220 for detecting pre-determined parameters of a well circulatory system. The sensors 220 may include a well flow-in sensor 226, flow-out sensor 228 and/or pit volume sensor 230. The system may also include a light source 106 configured to provide lighting during diverse weather conditions and times of day.

Additional embodiments of the system may include the speed and/or the speed and/or angle of the shaker table 206 being adjusted based on information received from the processor 110. Certain embodiments of the system may also include at least two cameras 102 which are configured to provide stereo vision. Other embodiments may additionally or alternatively include at least two cameras 102 configured to monitor the shaker table 206 from significantly different angles.

Some embodiments of the system may include a bit-depth sensor 232 and/or a database 112 for recording particle information. Certain embodiments may include a database 112 which is capable of comparing current data against historical data. The system may also include an alarm 114 for alerting staff or an operator to the occurrence of a pre-determined condition.

Certain embodiments related to a method for measuring the characteristics of drill cuttings. The method may include the steps of acquiring visual data 302 from at least one camera, compiling visual data from multiple sources 304, performing particle detection 306 using the data and a processor 110, extracting feature data 308 of any detected particles, recording the visual or feature data 310 for future reference, comparing the visual or feature data against a database of previously recorded data 312, displaying the visual or feature data 314 to staff and/or initiating or interrupting automated activity 318 using a machinery control system operably connected to the processor based on the extracted feature data.

Additional embodiments may relate to a system for monitoring characteristics of drilling cuttings exiting a shaker table. The system may include a shaker table screen 208, at least one camera 102 or distance sensing equipment 103 configured to monitor the shaker table screen 208. The camera 102 or distance sensing equipment 103 may be operably connected to a processor 110. The processor 110 may be configured to identify drill cuttings 104 and estimate the volume and/or characteristics of the cuttings 104 on the screen 208 using machine vision techniques.

Disclosed embodiments relate to a method for detecting or localizing a fluid front 118 on a shaker table 206. The method may include the steps of acquiring visual data 402 using at least one camera, compiling visual data from multiple sources 404, performing fluid front localization 406 using the data and a processor, recording data 408, comparing data against a database of previously recorded data 410, displaying data 412 and initiating, altering or interrupting automated activity 414 using a machinery control system operably connected to the processor based on the fluid front localization.

What is claimed is:

1. A computer vision system for monitoring cuttings from drilling, the computer vision system comprising:
   a camera oriented to face at least a portion of a screen surface of a shaker having drilling mud or cuttings thereon from a well during drilling;
   a processor coupled to the camera; and
   a memory coupled to the processor, wherein the memory comprises instructions executable by the processor to:
   acquire a first plurality of images from the camera;
   detect a first plurality of particles from the first plurality of images;
   obtain first particle data associated with the first plurality of images;
   model a first distribution of the first plurality of particles based at least in part on the first particle data associated with the first plurality of images;
   acquire a second plurality of images from the camera;
   detect a second plurality of particles from the second plurality of images;
   obtain second particle data associated with the second plurality of images;
   model a second distribution of the second plurality of particles based at least in part on the second particle data associated with the second plurality of images;
   determine a difference in a likelihood of a distribution of particles based at least in part on the first distribution and the second distribution; and
   provide an alert if the difference in the likelihood of the distribution of particles falls outside a threshold range.

2. The system of claim 1, wherein the first plurality of particles and the second plurality of particles each comprise a volume of cuttings per unit of time.

3. The system of claim 1, wherein the instructions are further executable by the processor to:
   initiate, inhibit, or interrupt a drilling activity if the difference in the likelihood of the distribution of particles falls outside the threshold range.

4. The system of claim 1, wherein the first distribution of the first plurality of particles is based at least in part on a density estimate of the first plurality of particles from the first plurality of images.

5. The system of claim 1, wherein the alert comprises a visual alert or a text message regarding the difference in the likelihood of the distribution of particles falling outside the threshold range.

6. The system of claim 1, wherein the instructions are further executable by the processor to:
   obtain historical data associated with a plurality of historical images from the camera acquired during drilling one or more previous wells; and
   identify one or more drilling conditions from the historical data.

7. The system of claim 6, wherein the instructions are further executable by the processor to:
   determine a drilling condition of the one or more drilling conditions has occurred based at least in part on the historical data and the difference in the likelihood of the distribution of particles falling outside the threshold range.

8. A method for monitoring cuttings from drilling, the method comprising:
   acquiring, by a computer vision system, a plurality of images from a camera oriented to face at least a portion of a screen surface of a shaker having drilling mud or cuttings thereon from a well during drilling;
   detecting, by the computer vision system, a plurality of particles from the plurality of images;
   obtaining, by the computer vision system, data associated with the plurality of particles;
   modeling, by the computer vision system, a statistical distribution of particles based at least in part on the data associated with the plurality of particles;
   monitoring, by the computer vision system, the statistical distribution of particles over time;
   determining, by the computer vision system, a change in a likelihood of the monitored statistical distribution of particles based at least in part on the modeled statistical distribution of particles; and
   providing, by the computer vision system, an alert if the change in the likelihood of the monitored statistical distribution of particles falls outside a threshold range.

9. The method of claim 8, wherein the plurality of particles comprises a volume of cuttings per unit of time.

10. The method of claim 8, further comprising:
    initiating, inhibiting, or interrupting a drilling activity if the change in the likelihood of the monitored statistical distribution of particles falls outside the threshold range.

11. The method of claim 8, wherein the statistical distribution of particles is based at least in part on a density estimate of the plurality of particles from the plurality of images.

12. The method of claim 8, wherein the alert comprises a visual alert or a text message regarding the change in the likelihood of the monitored statistical distribution of particles falling outside the threshold range.

13. The method of claim 8, further comprising:
obtaining, by the computer vision system, historical data associated with a plurality of historical images from the camera acquired during drilling one or more previous wells; and
identifying one or more drilling conditions from the historical data.

14. The method of claim 13, further comprising:
determining a drilling condition of the one or more drilling conditions has occurred based at least in part on the historical data and the change in the likelihood of the monitored statistical distribution of particles falling outside the threshold range.

15. A non-transitory computer readable storage medium comprising a plurality of instructions executable by one or more processors, the instructions comprising instructions which, when executed on the one or more data processors, cause the one or more data processors to perform actions including:
acquiring a plurality of images from a camera oriented to face at least a portion of a screen surface of a shaker having drilling mud or cuttings thereon from a well during drilling;
detecting a plurality of particles from the plurality of images;
obtaining data associated with the plurality of particles;
modeling a statistical distribution of particles based at least in part on the data associated with the plurality of particles;
monitoring the statistical distribution of particles over time;
determining a change in a likelihood of the monitored statistical distribution of particles based at least in part on the modeled statistical distribution of particles; and
providing an alert if the change in the likelihood of the monitored statistical distribution of particles falls outside a threshold range.

16. The non-transitory computer readable storage medium of claim 15, wherein the plurality of particles comprises a volume of cuttings per unit of time.

17. The non-transitory computer readable storage medium of claim 15, wherein the instructions further comprise instructions which, when executed on the one or more data processors, cause the one or more data processors to perform actions including:
initiating, inhibiting, or interrupting a drilling activity if the change in the likelihood of the monitored statistical distribution of particles falls outside the threshold range.

18. The non-transitory computer readable storage medium of claim 15, wherein the statistical distribution of particles is based at least in part on a density estimate of the plurality of particles from the plurality of images.

19. The non-transitory computer readable storage medium of claim 15, wherein the alert comprises a visual alert or a text message regarding the change in the likelihood of the monitored statistical distribution of particles falling outside the threshold range.

20. The non-transitory computer readable storage medium of claim 15, wherein the instructions further comprise instructions which, when executed on the one or more data processors, cause the one or more data processors to perform actions including:
obtaining historical data associated with a plurality of historical images from the camera acquired during drilling one or more previous wells;
identifying one or more drilling conditions from the historical data; and
determining a drilling condition of the one or more drilling conditions has occurred based at least in part on the historical data and the change in the likelihood of the monitored statistical distribution of particles falling outside the threshold range.

* * * * *